(12) United States Patent
Hancock, Jr.

(10) Patent No.: US 6,500,117 B1
(45) Date of Patent: *Dec. 31, 2002

(54) METHODS AND APPARATUS FOR INTERPRETING MEASURED LABORATORY DATA

(75) Inventor: William Franklin Hancock, Jr., 1303 W. Davis St., Burlington, NC (US) 27215-2149

(73) Assignee: William Franklin Hancock, Jr., Burlington, NC (US)

(*) Notice: Subject to any disclaimer, the term of this patent is extended or adjusted under 35 U.S.C. 154(b) by 137 days.

This patent is subject to a terminal disclaimer.

(21) Appl. No.: 09/611,583

(22) Filed: Jul. 7, 2000

Related U.S. Application Data

(63) Continuation-in-part of application No. 09/145,999, filed on Sep. 2, 1998, now Pat. No. 6,292,761.

(51) Int. Cl.$^7$ ................................................. A61B 5/00
(52) U.S. Cl. ............................ 600/300; 128/920; 702/19
(58) Field of Search .......................... 600/300, 301; 128/920–925, 897–899; 702/183–189, 19

(56) References Cited

U.S. PATENT DOCUMENTS

| | | | |
|---|---|---|---|
| 3,855,459 A | 12/1974 | Hakata | 235/154 |
| 4,527,240 A | 7/1985 | Kvitash | 364/415 |
| 5,007,283 A | 4/1991 | Ambos | |
| 5,371,694 A | 12/1994 | Kawawaki et al. | 364/709.16 |
| 5,541,854 A | 7/1996 | Yundt | 364/551.01 |
| 5,545,895 A | 8/1996 | Wright et al. | 250/282 |
| 5,616,504 A | 4/1997 | Brown et al. | 436/518 |
| 5,619,428 A | 4/1997 | Lee et al. | 364/551.01 |
| 5,731,998 A * | 3/1998 | Lotito et al. | 345/440 |
| 5,734,591 A | 3/1998 | Yundt | 364/551.01 |
| 5,993,388 A * | 11/1999 | Kattan et al. | 128/898 |
| 6,292,761 B1 * | 9/2001 | Hancock, Jr. | 345/440 |

FOREIGN PATENT DOCUMENTS

EP  0 753 283 A1  1/1997

OTHER PUBLICATIONS

Brochure, Normal distribution (mu,sigma), *http://www.cs.uni.edu/~campbell/stat/z–score.html* (1998).

Brochure, The International Temperature Scale of 1990 (ITS–90), Omega Engineering, Inc., *Omega.com*™ (1996).

Christensen, *Introduction to Statistics*, p. 149 (1992).

Wolf et al., *Interpretation of Biochemical Panels Utilizing Computer Analysis*, Clinical Biochemistry of Important Diseases, pp. 1–25 ((1986).

\* cited by examiner

Primary Examiner—Eric F. Winakur
Assistant Examiner—David McCrosky
(74) Attorney, Agent, or Firm—Myers Bigel Sibley & Sajovec

(57) ABSTRACT

Systems, methods, and computer program products for determining relative normalcy and abnormalcy of a plurality of test results are provided. Test results are transformed into respective unitized values and then graphically displayed with a unitized reference range. A unitized analytical variation of each of the respective unitized values may be determined and displayed. Unitized data can be graphically presented in a predefined order to produce patterns. These patterns can be compared, either manually or electronically, with other patterns representative of known conditions to quickly and easily assess the medical status of multiple body organs and/or systems of a patient, or to assess the condition of various attributes of objects including any type of process, product, machine, or system capable of being measured.

40 Claims, 9 Drawing Sheets

FIG. 4.

COMBINED UNITARY & TRADITIONAL REPORT

TRADITIONAL REPORT — UNITARY REPORT

BASIC METABOLIC PANEL SORTED

REFERENCE INTERVAL = 0.0 +/- 1.0

| TEST | MEASURED RESULT | | REFERENCE INTERVAL | UNITARY VALUE | | Bar (-3.0 to 3.0) |
|---|---|---|---|---|---|---|
| HYDRATION | | | | | | |
| SODIUM | L 131 | mE/L | 136 - 147 | -1.8 | L | -1.8 |
| CHLORIDE | L 93 | mEq/L | 97 - 109 | -1.5 | L | -1.5 |
| ALBUMIN | L 3.3 | g/dl | 3.4 - 5.3 | -1.1 | L | -1.1 |
| RENAL | | | | | | |
| CREATININE | LN 0.7 | mg/dl | 0.6 - 1.4 | -0.7 | LN | -0.7 |
| UREA NITROGEN | 17 | mg/dl | 7 - 24 | 0.2 | | 0.2 |
| ALBUMIN | L 3.3 | g/dl | 3.4 - 5.3 | -1.1 | L | -1.1 |
| BONE | | | | | | |
| PHOSPHATASE, ALK | 62 | IU/l | 23 - 140 | -0.3 | | -0.3 |
| CALCIUM | 9.4 | mg/dl | 8.9 - 10.8 | -0.5 | | -0.5 |
| LIVER | | | | | | |
| PROTEIN, TOTAL | 7.7 | g/dl | 6.1 - 8.2 | 0.5 | | 0.5 |
| TRANSFERASE (GOT) | H 70 | IU/L | 4 - 39 | 2.7 | H | 2.7 |
| PHOSPHATASE, ALK | 62 | IU/l | 23 - 140 | -0.3 | | -0.3 |
| BILIRUBIN, TOTAL | H 6.2 | mg/dl | 0.2 - 1.3 | 9.1 | H | 9.1 |
| METABOLISM | | | | | | |
| GLUCOSE | H 270 | mg/dl | 68 - 113 | 7.9 | H | 7.9 |
| ALBUMIN | L 3.3 | g/dl | 3.4 - 5.3 | -1.1 | L | -1.1 |
| PROTEIN, TOTAL | 7.7 | g/dl | 6.1 - 8.2 | 0.5 | | 0.5 |
| LYTES | | | | | | |
| SODIUM | L 131 | mE/L | 136 - 147 | -1.8 | L | -1.8 |
| CHLORIDE | L 93 | mEq/L | 97 - 109 | -1.5 | L | -1.5 |
| POTASSIUM | L 4.4 | mEq/L | 3.7 - 5.3 | -0.1 | L | -0.1 |

H = HIGH    L = LOW    LN = LOW NORMAL    HN = HIGH NORMAL

FIG. 5A.

HEMOGRAM 40

MV = MEASURED VALUE
MEASURED REFERENCE INTERVAL

HEMOGRAPH 42a
UV = UNITARY VALUE
UNITARY REFERENCE INTERVAL = 0.0 +/- 1.0

| TEST | MV | | RI | UV | | -3.0 | -2.0 | -1.0 | 0 | 1.0 | 2.0 | 3.0 |
|---|---|---|---|---|---|---|---|---|---|---|---|---|
| RBC | 3.10 x10⁸ | L | 4.10 - 5.60 | -2.3 | L | -2.3 | | | | | | |
| HGB | 10.1 g/dL | L | 12.5 - 17.0 | -2.0 | L | | -2.0 | | | | | |
| HCT | 31.3 % | L | 36.0 - 50.0 | -1.7 | L | | | -1.7 | | | | |
| MCV | 103 fl | H | 80 - 98 | 1.5 | H | | | | | 1.5 | | |
| MCH | 32.5 pg | HN | 27.0 - 34.0 | 0.6 | HN | | | | 0.6 | | | |
| MCHC | 31.7 g/dL | LN | 32.0 - 36.0 | -1.1 | LN | | | -1.1 | | | | |
| PLTS | 210 x10³ | | 140 - 415 | -0.5 | | | | | -0.5 | | | |
| WBC | 4.0 x10³ | L | 4.0 - 10.5 | -1.0 | L | | | -1.0 | | | | |
| %POLYS | 45 % | LN | 40 - 74 | -0.7 | LN | | | -0.7 | | | | |
| %LYMPHS | 38 % | | 14 - 46 | 0.5 | | | | | 0.5 | | | |
| %MONOS | 9 % | | 4 - 13 | 0.1 | | | | | 0.1 | | | |
| %Eos | 8 % | H | 0 - 7 | 1.1 | H | | | | | 1.1 | | |
| %BASOS | 0 % | LN | 0 - 3 | -0.8 | LN | | | -0.8 | | | | |
| POLYAbs | 1.7 x10³ | LN | 1.8 - 7.8 | -1.0 | LN | | | -1.0 | | | | |
| LYMPHAbs | 1.4 x10³ | LN | 0.7 - 4.5 | -0.6 | LN | | | -0.6 | | | | |
| MONOAbs | 0.3 x10³ | | 0.1 - 1.0 | -0.5 | | | | -0.5 | | | | |
| EOSAbs | 0.3 x10³ | | 0.0 - 0.4 | 0.4 | | | | | 0.4 | | | |
| BASOAbs | 0.0 x10³ | LN | 0.0 - 0.2 | -0.7 | LN | | | -0.7 | | | | |

L = LOW = <-1.0    H = HIGH = >1.0
LN = LOW NORMAL = -0.6 TO -1.0    HN = HIGH NORMAL = 0.6 TO 1.0
BLANK = MID NORMAL = 0.5 TO -0.5

HEMOGRAM 40

MV = MEASURED VALUE
RI = REFERENCE INTERVAL

| TEST | MV | | RI | UV | |
|------|-----|------|-----------|------|----|
| RBC  | 3.10 | x10⁶ | 4.10 - 5.60 | -2.3 | L |
| HGB  | 10.1 | g/dl | 12.5 - 17.0 | -2.0 | L |
| HCT  | 31.3 | %    | 36.0 - 50.0 | -1.7 | L |
| MCV  | 103  | fl   | 80 - 98     | 1.5  | H |
| MCH  | 32.5 | pg   | 27.0 - 34.0 | 0.6  | HN |
| MCHC | 31.7 | g/dl | 32.0 - 36.0 | -1.1 | L |

HEMOGRAPH 42b
UV = UNITARY VALUE
UNITARY REFERENCE INTERVAL = 0.0 +/- 1.0

| | -3.0 | -2.0 | -1.0 | 0 | 1.0 | 2.0 | 3.0 |
|---|---|---|---|---|---|---|---|
| RBC | -2.3 | | | | | | |
| HGB | | -2.0 | | | | | |
| HCT | | | -1.7 | | | | |
| MCV | | | | | | 1.5 | |
| MCH | | | | | 0.6 | | |
| MCHC | | | -1.1 | | | | |

L = LOW = <-1.0         BLANK = MID NORMAL = 0.5 TO -0.5         H = HIGH = >1.0
LN = LOW NORMAL = -0.6 TO -1.0                                    HN = HIGH NORMAL = 0.6 TO 1.0

*FIG. 5B.*

HEMOGRAM

MV = MEASURED VALUE
RI = REFERENCE INTERVAL

| TEST | | MV | | RI | UV | |
|---|---|---|---|---|---|---|
| RBC | LN | 3.85 | x10⁶ | 3.80 - 5.10 | -0.9 | LN |
| HGB | L | 8.1 | g/dL | 11.5 - 15.0 | -2.9 | L |
| HCT | L | 26.1 | % | 34.0 - 44.0 | -2.6 | L |
| MCV | L | 69 | fl | 80 - 98 | -2.1 | L |
| MCH | L | 21.5 | pg | 27.0 - 34.0 | -2.5 | L |
| MCHC | L | 31.6 | g/dL | 32.0 - 36.0 | -1.2 | L |

HEMOGRAPH 44
UV = UNITARY VALUE
UNITARY REFERENCE INTERVAL = 0.0 +/- 1.0

| | -3.0 | -2.0 | -1.0 | 0.0 | 1.0 | 2.0 | 3.0 |
|---|---|---|---|---|---|---|---|
| RBC | | | -0.9 | | | | |
| HGB | -2.9 | | | | | | |
| HCT | | -2.6 | | | | | |
| MCV | | -2.1 | | | | | |
| MCH | | -2.5 | | | | | |
| MCHC | | | -1.2 | | | | |

L = LOW = <-1.0
LN = LOW NORMAL = -0.6 TO -1.0
BLANK = MID NORMAL = 0.5 TO -0.5
H = HIGH = >1.0
HN = HIGH NORMAL = 0.6 TO 1.0

*FIG. 6A.*

HEMOGRAM

MV = MEASURED VALUE
RI = REFERENCE INTERVAL

| TEST | | MV | | RI | UV |
|---|---|---|---|---|---|
| RBC | L | 2.99 | x10⁶ | 3.80 - 5.10 | -2.2 L |
| HGB | L | 9.0 | g/dL | 11.5 - 15.0 | -2.4 L |
| HCT | L | 27.0 | % | 34.0 - 44.0 | -2.4 L |
| MCV | | 88 | fl | 80 - 98 | -0.1 |
| MCH | | 30.3 | pg | 27.0 - 34.0 | -0.1 |
| MCHC | | 33.7 | g/dL | 32.0 - 36.0 | -0.1 |

HEMOGRAPH 46

UV = UNITARY VALUE
UNITARY REFERENCE INTERVAL = 0.0 +/- 1.0

| | -3.0 | -2.0 | -1.0 | 0.0 | 1.0 | 2.0 | 3.0 |
|---|---|---|---|---|---|---|---|
| RBC | | -2.2 | | | | | |
| HGB | | -2.4 | | | | | |
| HCT | | -2.4 | | | | | |
| MCV | | | | -0.1 | | | |
| MCH | | | | -0.1 | | | |
| MCHC | | | | -0.1 | | | |

L = LOW = <-1.0          BLANK = MID NORMAL = 0.5 TO -0.5          H = HIGH = >1.0
LN = LOW NORMAL = -0.6 TO -1.0                                      HN = HIGH NORMAL = 0.6 TO 1.0

FIG. 6B.

METHODS AND APPARATUS FOR INTERPRETING MEASURED LABORATORY DATA

RELATED APPLICATIONS

This application is a continuation-in-part of U.S. patent application Ser. No. 09/145,999, now U.S. Pat. No. 6,292,761 filed on Sep. 2, 1998, which is hereby incorporated herein in its entirety by reference.

FIELD OF THE INVENTION

The present invention relates generally to data analysis and, more particularly, to reporting and comparison of data analysis results.

BACKGROUND OF THE INVENTION

The method of reporting numerical laboratory test data, such as biological and other laboratory tests, has essentially remained unchanged since its modern inception, beginning in the first half of the twentieth century. The traditional method includes reporting a measured value (i.e., a test result) and its relevant set of normal values, known as a reference range. It is often inadequate to report only a measured value because different tests may have different respective reference ranges. Generally, all reference ranges include a set of two values with one value designated as an upper reference range limit and another designated as a lower reference range limit.

In the last quarter of the twentieth century the number of available laboratory tests has risen prodigiously and there are now many hundreds of numerically reported tests, each continuing to have its own unique set of reference ranges. This marked proliferation of data has offered an interpreter of the data an abundant variety of tests from which to conduct physiological as well as disease investigations. However, the sheer volume of available tests has also contributed to information overload. An interpreter typically attempts to remember hundreds of reference ranges when evaluating test data. For example, a single composite tabular listing of lab results on one biological entity (or non-biological entity) can include forty or more tests, all of which may have different reference ranges.

Another aspect of the interpretation and application of measured biological (or non-biological) laboratory data is the observation that a test value that falls within the reference range has variable significance depending on whether the measured value is near the upper limit, the lower limit, or the mean value of the reference range. The relative significance of a test has to be qualitatively assessed and committed to memory because it is not typically quantified on the traditional report. If multiple tests are simultaneously reported, an interpreter of the test data typically tries to retain in his/her memory the relative position of each measured value and make qualitative interpretive decisions among the tests utilizing mentally calculated relative positions in the reported test data. For example, one test may have a measured value two points below the upper reference range value and another test may have a measured value eight points below the upper reference range value. The interpreter may wish to know if one of these tests is at more risk for being abnormally elevated than the other test. A qualitative evaluation may be required because the number of points in the reference range for each of these tests may be different. The relative closeness of one value to the upper reference range (or the lower reference range for that matter) may be dependent on the number of units in the reference range. Table 1 below illustrates this situation.

TABLE 1

| Test | MV = −2 | MV = −8 | Reference Range |
|---|---|---|---|
| Sodium | 145 | 139 | 136–147 |
| Glucose | 111 | 105 | 68–113 |
| Cholesterol | 198 | 192 | 100–200 |

In Table 1, the second column (MV=−2) indicates a measured value two numbers less than the upper limit of the reference range. The third column (MV=−8) indicates a measured value eight numbers less than the upper limit of the reference range. Each of the six measured values (MVs) in Table 1 are considered normal values because each lies within the reference range for a respective test. When measured values are viewed in the format of Table 1, which resembles traditional reporting formats, it may be difficult to determine which measured value is relatively greater than, or less than, any other measured value.

Consequently, if measured values that fall within a reference range are to be compared among the many different tests, then an interpreter should perform a qualitative analysis on each test and retain this information in memory for each test. If this type of mental calculation is not performed, then refinement in the application of measured values may not be possible and diagnostic information may be lost.

The concept of relative normalcy of a measured value that falls within a reference range is also applicable to measured abnormal values that are above or below a reference range. The same qualitative mental assessment is involved in determining the relative abnormalcy of an abnormal value. An example of this would be to determine whether a liver function test that is elevated ten points above the upper reference range is as qualitatively elevated as another liver function test that is also ten points above the upper reference range. Since these two tests may indicate different parts of the liver, it is reasonable to ask whether one part of the liver is more diseased than the other. This process of test comparison may become even more complex when the interpreter is attempting to assess a panel of many tests that relate to different organs or different diseases. This type of analysis is generally referred to as multiparametric analysis.

There have been attempts to present multiparametric test data from biological entities in a non-traditional format in order to enhance an interpreter's perception of inter-test relationships and abnormal values. For example, U.S. Pat. No. 4,527,240 to Kvitash describes a process whereby measured patient values are transformed to units referred to as "Balascopic" units. Unfortunately, in data analysis according to Kvitash, the Balascopic units are plotted on an axial graph. These axial graphs may be somewhat difficult to use. Furthermore, the Balascopic process of Kvitash does not distinguish between test data reported as whole integers and decimals. Consequently, interpretative decisions that are made based on decimal values may be difficult to make with the Kvitash process. Another drawback of the Kvitash process is that it does not provide analytical variation associated with each measured value.

U.S. Pat. No. 5,541,854 to Yundt describes displaying conventional multi-level hematology quality control data (three levels) in a complex graphic form. Yundt is concerned with the presentation of tri-level quality control data and not with the presentation of measured unknown samples.

Statistical methods utilizing "Z scores" to specify the relative frequency or probability of a random number in a normally distributed set of measurements are known. Unfortunately, Z scores are somewhat difficult to use to identify the relative value of one test result to another. Furthermore Z score techniques are somewhat limited because data beyond the maximum and minimum limits of normal distribution cannot be used.

SUMMARY OF THE INVENTION

In view of the above discussion, it is an object of the present invention to reduce much of the complexity associated with interpreting laboratory test data.

It is another object of the present invention to facilitate determining relative relationships of measured values from laboratory tests to respective reference ranges.

These and other objects are provided by systems, methods, and computer program products for determining relative normalcy or abnormalcy (or any other type of variation) of a plurality of test results, by transforming test results into respective unitized values and then graphically displaying each of the unitized values with a unitized reference range. Additionally, a unitized analytical variation of each of the respective unitized values may be determined and displayed.

Initially, a reference range for a test is unitized to a single number. A total number of possible test results within respective portions (e.g., halves) of the reference range is then determined. This is accomplished by determining a total number of possible test results within the reference range to produce a reference range spread, and then dividing the reference range spread in portions.

The fractional value of the plurality of test results in the respective portions of the reference range is then determined. The fractional value of the plurality of test results comprises a reciprocal of the total number of possible test results in the portion of the reference range. Each of the plurality of separately determined test results are then transformed into respective equilibrated values. This is accomplished by determining the equilibration point of the reference range and then determining a difference between the equilibration point and each of the plurality of test results. Each equilibrated value represents a relative position of a respective test result with respect to an equilibration point of the reference range.

Each of the equilibrated values is then transformed into respective unitized values by multiplying each respective equilibrated value with a respective fractional value of the plurality of test results in the portion of the reference range. Each unitized value represents relative normalcy or abnormalcy of a respective test result with respect to the unitized reference range.

According to the present invention, unitized values with the same numerical value indicate the same quantitative variation from any reference point(s) within the unitized reference range. According to the present invention, a unitized value of 1.5 for a glucose level within a patient and a unitized value of 1.5 for a sodium level within a patient will mean the same quantitative increase for each test. Furthermore, the present invention may allow an interpreter to recognize problems and undertake corrective actions sooner. By utilizing unitized values according to the present invention, an interpreter could more easily recognize that a unitized sodium value of 1.5 is more severe than a unitized glucose value of 1.1 and, therefore, take action to rectify the sodium level.

According to another embodiment of the present invention, unitized data can be graphically presented in a predefined order to produce patterns. These patterns can be compared, either manually or electronically, with other patterns representative of known medical conditions to quickly and easily assess the medical status of multiple body organs and/or systems of a patient.

The present invention may be applied to the interpretation of any type of laboratory test data, both biological and non-biological, and particularly where the test data is interpreted by referring to a reference range. Furthermore, the present invention may be applied to the interpretation of data measured from any entity, system, or process which is capable of being measured, including biological and non-biological entities. The present invention is particularly useful where multiparametric data is obtained from testing.

BRIEF DESCRIPTION OF THE DRAWINGS

FIG. 4 illustrates medical test results in both a traditional reporting format and in a graphical representation of the unitized format, according to the present invention.

FIG. 5A contains a listing (hemogram) of test results and unitized test values for various medical tests and a bar graph representation (hemograph) of the unitized test values which forms a recognizable pattern according to the present invention.

FIG. 5B illustrates the unitized data of FIG. 5A in bar graph format with each bar extending in the same direction to form a recognizable pattern according to the present invention.

FIGS. 6A and 6B illustrate hemographs that have distinct patterns indicating the existence of microcytic anemia and normocytic anemia, respectively.

DETAILED DESCRIPTION OF THE INVENTION

Figure 1:
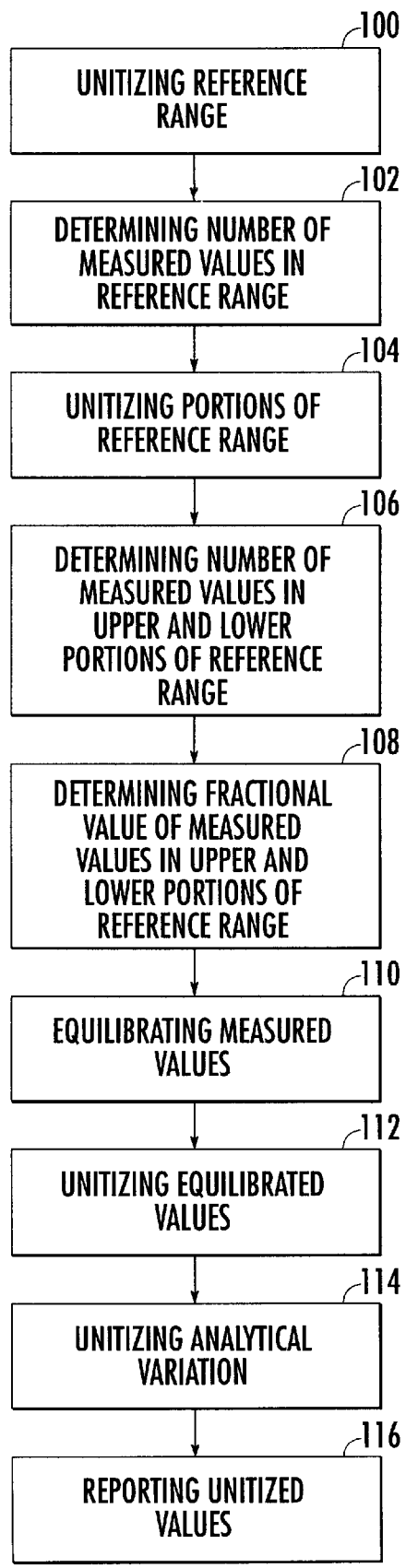
FIG. 1 schematically illustrates operations for unitizing test data having different reference ranges, according to an embodiment of the present invention.

The present invention now is described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

As will be appreciated by one of skill in the art, the present invention may be embodied as a method, data processing system, or computer program product. Accordingly, the present invention may take the form of an entirely hardware embodiment, an entirely software embodiment or an embodiment combining software and hardware aspects. Furthermore, the present invention may take the form of a computer program product on a computer-readable storage medium having computer-readable program code embodied in the medium. Any suitable computer readable medium may be utilized including hard disks, CD-ROMs, optical storage devices, or magnetic storage devices.

The present invention is described below with reference to flowchart illustrations of methods, apparatus (systems) and computer program products according to an embodiment of the invention. It will be understood that each block of the flowchart illustrations, and combinations of blocks in the flowchart illustrations, can be implemented by computer program instructions. These computer program instructions may be loaded onto a general purpose computer, special purpose computer, or other programmable data processing apparatus to produce a machine, such that the instructions which execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Accordingly, blocks of the flowchart illustrations support combinations of means for performing the specified functions, combinations of steps for performing the specified functions and program instruction means for performing the specified functions. It will also be understood that each block of the flowchart illustrations, and combinations of blocks in the flowchart illustrations, can be implemented by special purpose hardware-based computer systems which perform the specified functions or steps, or combinations of special purpose hardware and computer instructions.

Referring now to FIG. 1, operations for unitizing test data having different reference ranges, according to an embodiment of the present invention, are schematically illustrated. Operations include: unitizing a reference range (Block 100); determining the number of measured values in the reference range (Block 102); unitizing portions of the reference range (Block 104); determining the number of measured values in upper and lower portions of the reference range (Block 106); determining the fractional value of the measured values in the upper and lower portions of the reference range (Block 108); equilibrating the measured values (Block 110); unitizing the equilibrated values (Block 112); unitizing the analytical variation (Block 114); and reporting the unitized values (Block 116). Each of these operations will be described in detail below.

It is understood that operations according to the present invention are not limited to multiparametric analysis of a living being (e.g., a biological entity such as a human being or an animal). The present invention may be utilized with multiparametric analysis of non-biological entities including, but not limited to, machines, processes, products, and systems. Hereinafter, the term "object" shall be understood to include any entity, system, product, machine, or process which is capable of being measured including biological and non-biological entities. For example, the present invention may be utilized with various tests performed on a metal object to assess the conditions of different attributes (e.g., hardness, ductility, chemical composition, fracture toughness, and the like) of the metal part. For example, a measurable condition of the attribute "ductility" of a material includes "elongation." Elongation is generally determined by subjecting a material to tensile forces and measuring the elongation the material is capable of undergoing before the occurrence of fracture.

Figure 2:
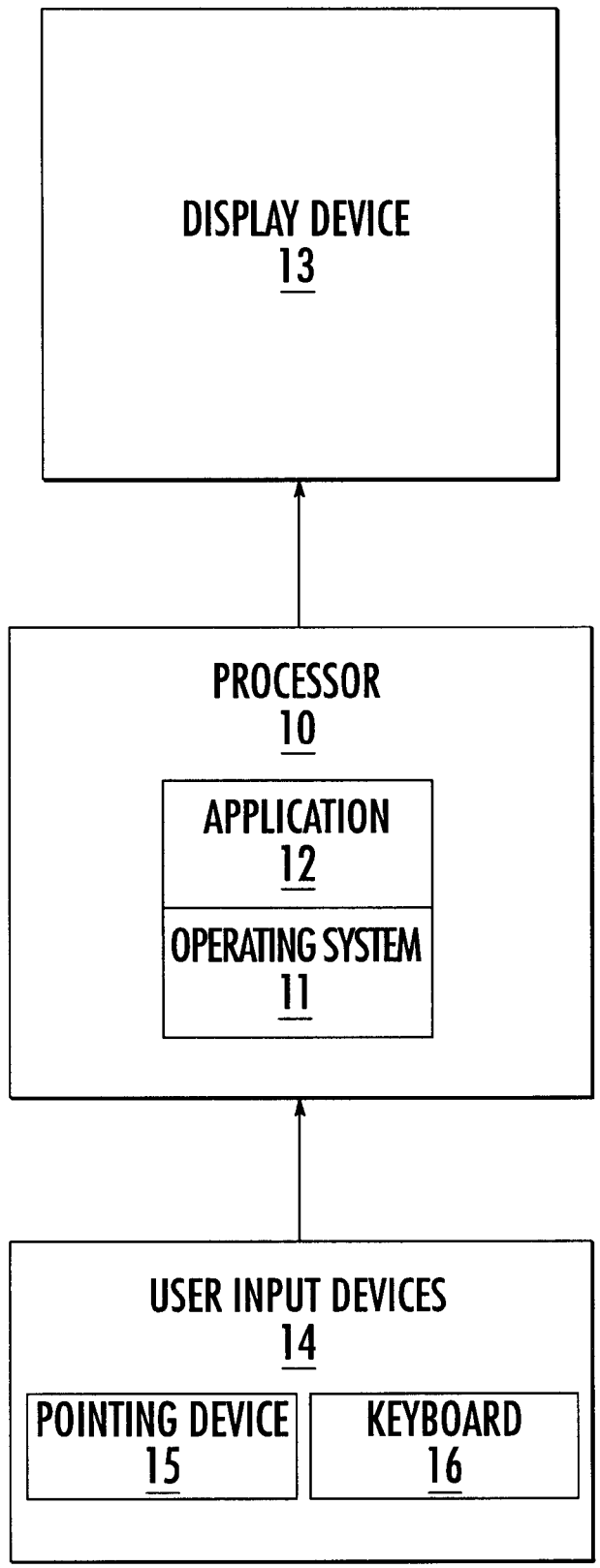
FIG. 2 illustrates an exemplary data processing system in which the present invention may be implemented.

Referring now to FIG. 2, an exemplary data processing system in which the present invention may be implemented is illustrated. As seen in FIG. 2, a data processor 10 may have an operating system 11 resident therein. An application program 12 for performing operations according to the present invention typically executes via the operating system 11. The processor 10 displays information on a display device 13 which has a plurality of picture elements (collectively referred to as a screen). The information is displayed on the display device 13, preferably with a graphical user interface. The contents of the screen of the display device 13 and the appearance of a graphical user interface may be controlled or altered by an application program 12 or the operating system 11 either individually or in combination. For obtaining input from a user, the operating system 11 and the application program 12 may utilize user input devices 14. User input devices 14 may include a pointing device 15, such as a mouse, and a keyboard 16 or other input devices known to those of skill in the art.

Table 2 below defines abbreviations used throughout this disclosure.

TABLE 2

| Abbreviation | Definition |
| --- | --- |
| EV | equilibrated value |
| FV | fractional value |
| HRRS | half reference range spread |
| LRRL | lower reference range limit |
| MV | measured value |
| RR | reference range |
| RRS | reference range spread |
| UAV | unitized analytical variance |
| URRL | upper reference range limit |
| UV | unitized value |

It is understood that the term "measured value" as used herein is synonymous with the term "test result", such as a blood glucose level produced by a blood test, or a hardness value for a material produced by a hardness tester for materials.

Unitizing a Reference Range

An initial operation of the present invention involves unitizing a reference range (Block 100). Unitization of a reference range is defined as grouping all measured values for each laboratory (or other) test within a reference range into a single number. By way of explanation, inherent in the definition of a RR is the possibility that any MV that falls within a RR is as potentially normal, in an equivalent biological (or non-biological) sense, as any other MV within the same RR, or any other RR. Since this potential exists, it is conceptually feasible to consider all MVs in any RR as equivalent values. As a derivative of this consideration, all of the MVs in any RR can be conceptually consolidated into one number which would have no need of any assigned concentration units.

For example, if the number 1.0 is selected, the reference range may be any value greater than 0.0 and equal to or less than 1.0, since this comprises the number 1.0. However, it is to be understood that any number can be used for this purpose. From this concept, it does follow that if one test has a MV of 100 milligrams per deciliter (mg/dl) in its RR and another test has a MV of 10 millimoles per liter (mmol/L) in its RR, these different MVs lose the concentration units (mg/dl and mmol/L); and, the 100 MV and the 10 MV are biological equivalents. This conceptual process is an initial necessary process in order to restructure the ordinarily disparate MVs in RRs into one number. The equation that expresses this relationship is $$0.0 < \text{Unitized } RR < 1.0 \qquad \text{(Equation 1)}$$

Equation 1 states that a unitized RR is greater than zero but less than or equal to one.

Determining the Number of Measured Values in the Reference Range

Next a determination of the number of measured values that are included in the reference range from the lower reference range limit to, and including, the upper reference range limit is made (Block 102). The number of measured values in this range is determined by both the unique analytical properties of the test and by the actual measured values discovered in the reference (normal) population, and represents a fixed number of MVs peculiar to each test and the methodology used in the testing procedure. The RR is not only different for each test, but the RR will also change for any given test if the methodology for that test is changed, which further adds to the memory requirements of an interpreter and the need for advance notice by a laboratory when methodology is changed. The number of MVs within the RR is calculated from the high and low numbers listed under the heading "Reference Range", or sometimes otherwise described as "Reference Interval" or "Normal Range". The total number of measured values in the reference range spread is preferably determined by Equation 2 below.

$$RRS = (URRL - LRRL) + 1 \qquad \text{(Equation 2)}$$

The URRL and LRRL, when used in Equation 2, refer to the numbers given in a traditional report (e.g., Table 1 above) under the heading of RR, and not to the unitized reference range of 1.0.

Equation 2 includes all units in the reference range by the addition of a whole integer to the difference between the minimum and maximum of the reference range. For example, the RR for glucose may be given as 68—113 mg/dl. Since the UV will be unit-less, the concentration units of mg/dl can be dropped. Under this arrangement the URRL=113 and the LRRL=68. The RR numbers are then inserted into Equation 2, as follows:

$$RRS = (113 - 68) + 1$$
$$= 45 + 1$$
$$= 46$$

In the process of eventually converting measured values to unitized values, all reported decimal values in the reference ranges and all measured values reported in decimals need to be converted to their equivalent whole values. For example a reference range of 4.6–8.7 is converted to 46–87 and the number of MVs in the RRS is (87−46)+1=42. Measured decimal values are also converted to their equivalent whole numbers. All subsequent calculations are performed on the converted whole numbers. This modification is required because the interpreter would have most likely used "tenths" of a number in evaluating increases or decreases in measured values. Once decimal values are converted to their equivalent whole numbers, the subsequently calculated UV reflects the original MV as it was expressed in tenths, or other decimal points.

The traditionally given upper and lower limits of a RR represent ±2 standard deviations of the MVs from the mean of the normal population studied, which includes only 95% of the MVs of the normal population. The 5% that are not included in the RR are represented by a deletion of 2.5% at both the upper and lower limits of the RR. Consequently, the determination of the RRS does not include the 2.5% of the MVs at either extreme of the RR. A total number of the MVs in the RRS could be determined by returning the deleted 5% to the RRS; however, since interpreters of MVs are conditioned to interpreting MVs on the traditional basis of a RR defined as ±2 standard deviations from the mean, the calculation for the total RRS is not incorporated herein.

Unitizing Portions of the Reference Range

The initial unitization of the reference range and the subsequent determinations of the RRS need to be restructured for the following reason. A low abnormal measured value, subsequently unitized to −0.5 would be the analytical equivalent, in the opposite direction, of a high abnormal unitized value of +1.5, since both values would be a 0.5 units beyond the lower and upper limits, respectively, of the unitized reference range. In a reporting format a reviewer would find these equidistant analytical values disconcerting since they are different numbers.

The above anomaly can be rectified by dividing the reference range into portions (e.g., halves) and then unitizing the separate components (Block 104). The mean of the reference range then becomes 0.0. The range from the mean to the LRRL is defined as 0.0 to −1.0. The range from the mean to the URRL is defined as 0.0 to +1.0. However, as was indicated in the initial unitization of the reference range, any number can be used. For purposes of this discussion, the number 1.0 is retained, but modified to −1.0 and +1.0 for the halves of the reference range spread. It is also understood that the reference range can be divided into quartiles, or other divisions, in order to cause the unitized values to be distributed in a manner to allow a desired distribution of the unitized values. However, for purposes of illustration herein, the reference range will be divided into halves. It is understood that the term "portion of a reference range" is intended-to mean all of a reference range or any divisible part of a reference range, such as halves, quartiles, and the like.

Determining the Number of Measured Values in Upper and Lower Halves of Reference Range Because the RR is divided into halves, the previously calculated number of MVs in the RRS (Equation 2) needs to be divided between the two halves. The number of MVs in each half of the RRS can be determined by the following equation:

$$HRRS = RRS/2 \qquad \text{(Equation 3)}$$

For example, the HRRS for glucose is:

$$HRRS=46/2=23$$

Determining the Fractional Value of the Measured Values in the Upper and Lower Halves of the Reference Range One of the components of the equation used to calculate UVs is the fractional value (FV). FV is defined as the reciprocal value of the MVs that are present in the HRRS. The fractional value of each of the measured values in the HRRS is determined by Equation 4, when the number 1.0 is used to represent one half of the reference range. If a number other than 1.0 is used to represent the specified division of the reference range, then this other number is substituted for 1.0.

$$FV=1/HRRS \quad \text{(Equation 4)}$$

For example, the FV for glucose is:

$$FV=1/23=0.04$$

The FV can be expressed as either a fraction or a percent.

The division of the RRS into two halves, each containing 2 standard deviations of the normal distribution is based on the conventional definition of normalcy as ±2 standard deviations of the mean. It would be feasible to unitize on the basis of +1 standard deviation from the mean which would define the unitary values in synchrony with unitary divisions of the standard deviations. For example +1 standard deviation would equal +1.0 unit, -1 standard deviation would equal -1.0 unit; +2 standard deviations would equal +2.0 units; and, -2 standard deviations would equal -2.0 units. This additional separation of the reference range brings greater sensitivity to the process, and fractional values can be proportioned accordingly.

Alternatively, it would also be feasible to unitize on the basis of ±3, or more, standard deviations per halves of the RR. This contraction of the reference range would reduce the sensitivity of the process, if this were desired. However, these extended processes are not performed herein because the traditional definition of normalcy is ±2 standard deviations from the mean.

Equilibrating Measured Values

Prior to the conversion of a measured value to a unitized value, the measured value needs to be equilibrated with the mean (or other equilibration point) of the reference range (Block 110), since the mean now represents zero. (In the traditional reporting process, zero is the value assigned to no detectable analyte levels.) This is accomplished by removing from the measured value the same number of units that were removed in converting the mean to zero. Equation 5 below illustrates the conversion of the measured value (MV) to an equilibrated value (EV).

$$EV=MV-MEAN \quad \text{(Equation 5)}$$

Fundamental to this concept is that equilibrated values less than the mean will show increasingly more negative values, whereas equilibrated values above the mean will show increasingly more positive values. For example, the mean of the RR for glucose is (68+113)/2=90.5, rounded to 91. A MV of 71 would have an EV of 71-91=-20; a MV of 91 would have an EV of 91-91=0; and, a MV of 111 would have an EV of 111-91=+20. Because the + or - EV will be multiplied by the always positive FV in a subsequent step to obtain the UV, the UV will carry the same + or - sign that the EV carried.

A "point of equilibration" is defined as a value, preferably in the reference range, from which measured values diverge. In the examples set forth herein, the point of equilibration is usually the "mean". However, other values may be chosen, such as 0.0, as used in an example below.

Unitizing the Equilibrated Values

Once a measured value has been equilibrated (Block 110), the result can be unitized by determining the number of unitized values (UVs) that are present in the equilibrated values (Block 112). Equation 6 illustrates how to determine the unitized value (UV) of an equilibrated value (EV).

$$UV=EV \times FV \quad \text{(Equation 6)}$$

Utilizing the operations of Block 100-Block 112, all of the different tests that were measured can be converted to UVs. All of the tests will now be fractions, or multiples, of the unitized upper or lower halves of the reference range. All measured values will be proportionately represented in comparison to one another. For example, a unitized value of +0.25 may represent a 40 measured value for one test and a 20 measured value for another test. However, when these measured values are unitized they could both represent +0.25 and the interpreter would then very quickly make a judgment of analytical equivalence between these two measured results.

Although analytical equivalence of two (or more) tests is indicated by the same unitized value, it does not follow that these equivalent values connote the same priority of urgency to the interpreter. For example, equivalent unitized values for potassium and alkaline phosphatase do not obviate the greater sense of immediate concern for illness that the evaluation of an elevated unitized potassium value brings when judged against an analytically equivalent elevated unitized alkaline phosphatase value. However, the interpreter is now free to make decisions without having to deal with the ambiguity of visually non-equivalent reported values. This reporting of unitized values eliminates the need for the interpreter to make mental calculations from the traditional report on the relative position of any measured value (raw data) to its reference range. All tests will now be proportionately equivalent. The interpreter can assess whether a glucose of +1.5 is medically more critical than a creatinine of +1.5 without having to do mental calculations on the relative deviation of the measured value from the upper reference range.

Occasionally, it may be desirable to standardize MVs without division of the reference range into halves. In these instances the abnormal values may be stated to be above or below a limiting value (LV). The herein-described unitary method can accommodate this consideration by eliminating Equation 3 and substituting a different reference point for the MEAN in Equation 5.

For example, if it is stated that values above 10 are abnormal, and a MV of 12 is determined, UVs can be calculated in the following manner. The RRS is calculated in the usual manner on the basis that any value equal to or less than 10 is normal. The number "1" is chosen as a lower limit, although it is understood that any value greater than zero and less than 1.0 can be used.

$$RRS = (10-1)+1$$

$$= 10$$

Since the RRS is not divided into halves, Equation 3 is skipped, and the FV is calculated in the usual manner.

$$FV = 1/10$$
$$= 0.1$$

In the subsequent equilibration step of Equation 5, 0.0 is substituted for the mean.

$$EV = MV - 0.0$$
$$= 12 - 0.0$$
$$= 12$$

The UV is then calculated in the usual manner.

$$UV = EV \times FV$$
$$= 12 \times 0.1$$
$$= 1.2$$

The interpretative guidelines for the UV in this instance would be that all values greater than 1.0 are abnormal and all values equal to or less than 1.0 are normal.

Alternatively, the MVs could be standardized on the basis of 10, instead of 1, in which case the $$FV = 10/RRS$$
$$= 10/10$$
$$= 1.0$$

and the $$UV = FV \times EV$$
$$= 1.0 \times 12$$
$$= 12$$

The interpretative guidelines for the UV in this example would be that all values greater than 10.0 are abnormal and all values equal to or less than 10.0 are normal.

These examples are provided in order to demonstrate that the herein described method can eliminate a specific step (division into halves) and substitute the reference point from which MVs diverge (the mean in prior examples) with another point (0.0 in this example) in order to accommodate different preferred definitions of the reference range, without altering the primary premise (Equation 1) that all numbers in the reference range are conceptually equivalent. Furthermore, the subsequently derived UVs remain standardized and proportionate to one another herein.

EXAMPLE 1

The measured values obtained from two different biological laboratory tests (i.e., sodium and glucose levels) are set forth below in Table 3. These MVs will be processed according to the operations represented by Blocks 100–112 described above. The resulting unitized values are tabulated in Table 4.

TABLE 3

| Test | MV#1 (−2) | MV#2 (−8) | MV#3 (+8) | Reference Range |
|---|---|---|---|---|
| Sodium | 145 | 139 | 155 | 136–147 |
| Glucose | 111 | 105 | 121 | 68–113 |

In Table 3, MV#1, MV#2, and MV#3 are −2, −8, and +8, respectively, from the upper limit of the reference range.
1) Unitize reference range: 0.0–1.0
2) Determine number of MVs in reference range:
   Sodium=147−136+1=12
   Glucose=113−68+1=46
3) Determine number of MVs in upper and lower halves of reference range:
   Sodium=12/2=6
   Glucose=46/2=23
4) Determine fractional value of MVs in upper and lower halves of reference range:
   Sodium=1/6=0.17
   Glucose=1/23=0.04
5) Convert each MV to an equilibrated value (EV):
   Sodium: Mean=(136+147)/2=142
   Glucose: Mean=(68+113)/2=91
Sodium:
   EV#1=MV#1−Mean=145−142=3
   EV#2=MV#2−Mean=139−142 −3
   EV#3=MV#3−Mean=155−142=13
Glucose:
   EV#1=MV#1−Mean=111−91=20
   EV#2=MV#2−Mean=105−91=14
   EV#3=MV#3−Mean=121−91=30
6) Unitize equilibrated values:
Sodium:
   UV#1=EV#1×FV=3×0.17=0.51
   UV#2=EV#2×FV=−3×0.17=−0.51
   UV#3=EV#3×FV=13×0.17=2.21
Glucose:
   UV#1=EV#1×FV=20×0.04=0.80
   UV#2=EV#2×FV=14×0.04=0.56
   UV#3=EV#3×FV=30×0.04=1.20

TABLE 4

| Test | MV#1 (−2) | UV#1 | MV#2 (−8) | UV#2 | MV#3 (+8) | UV#3 |
|---|---|---|---|---|---|---|
| Sodium | 145 | 0.51 | 139 | −0.51 | 155 | 2.21 |
| Glucose | 111 | 0.80 | 105 | 0.56 | 121 | 1.20 |

From the unitized data, an interpreter can readily determine that a sodium value of 145 (a −2 MV) with a UV of 0.51 is essentially the analytical equivalent of a glucose value of 105 (a −8 MV) with a UV of 0.56. Similarly, an interpreter can quickly observe that a sodium value of 139 (a −8 MV) is significantly different from a glucose of 105 (also a −8 MV), which have UVs of −0.51 and 0.56, respectively.

The traditional method of reporting laboratory data, as seen in Table 4 under the columns giving the MVs, does not allow one to determine the relative relationships that can be readily perceived by evaluating the unitized values seen in the columns listing the UVs. After many years of interpreting the traditionally reported raw data (MVs), users may develop variably refined cognitive perceptions of relative normalcy and abnormalcy of MVs. However, with the reporting of UVs, the relative normalcy and abnormalcy are quantified on the report and a new user will more quickly develop a refined capacity to engage in multiparametric analyses, with sundry benefits to the diagnostic process(es), many years prior to that learned by only utilizing the current state of the art.

Unitizing the Analytical Variation

All measured values have a degree of analytical variability, due to imprecision that is inherent in all laboratory and other testing instruments and the reagents used to determine the MVs. This variation is determined by running controls of known values with the samples from which measured values are determined. The analytic variation of control samples are usually subjected to statistical analysis wherein means and standard deviations are calculated. Often the mean is divided into one standard derivation to yield a value defined as the coefficient of variation. In conventional reports neither the standard deviation nor the coefficient of variation are reported with the measured value. The only values traditionally reported with measured values are the URRL and the LRRL, which constitute the reference range. If the analytical variations were available, the interpreter would be better able to make interpretive judgments on measured values that are near the URRL and the LRRL.

In most analytical systems at least two levels of known control are measured, in order to assess the analytical variability of the testing system near its lower and upper linear limits. The control closest to the measured value may be the most applicable value; however, in practice it may be a complex process to align the measured value and the closest control value. The average of the standard deviations of the controls can be used. The standard deviations of the controls are traditionally calculated from the MVs of the controls in such a manner that they do not need to be equilibrated. Since there is no need to perform the equilibration step on the standard deviation of the control value, and the FV has already been calculated, the conversion of the unitized analytical variation (Block 114) (UAV) may be accomplished by Equation 7.

$$\pm UAV = \pm \text{Standard Deviation} \times FV \quad \text{(Equation 7)}$$

Instead of using the standard deviation(s) of the control values as the measure of the analytical variability of a testing system, other measures of variance can be used and could include the entities of 1) the mean absolute deviation from the mean, or 2) the mean deviation from the median, or 3) any other useful approach to determining variance. Due to the traditional use of standard deviations to express the analytical variability of the control values, the standard variation is used herein.

These other possible methods which can be used to determine variance for controls may also be used to determine reference ranges for measured values, instead of the traditional mean plus or minus (+/−) two standard deviations. It is preferable that the same method used for determining variance of the controls be used to determine the reference ranges. Regardless of the method used to determine variance of the controls or to determine the reference range, the method described herein to determine UV can be used.

Reporting the Unitized Values

The following eight examples represent formats that can be used in reporting the unitized values, as well as traditional values (Block 116). The MVs, RRs and the standard deviations (used to calculate the UAVs) set forth below are representative and not specific to an individual, a particular testing system, or a designated lab site.

EXAMPLE 2

This is a traditional report in which the abnormal measured values have been accentuated for instant recognition. The abnormal values have been notated as HI or LO. Abnormal values may also be printed in bold, offset or printed in a different color in order to alert an interpreter to the abnormal value. The tests are listed alphabetically. They are not ranked by high or low values because the data in this traditional report does not allow the interpreter to determine the relative value among the various tests.

| TRADITIONAL REPORT | | | |
|---|---|---|---|
| TEST | RESULT | | REFERENCE RANGE |
| Albumin | LO | 3.3 g/dL | 3.4–5.3 |
| Bilirubin, total | HI | 6.2 mg/dL | 0.2–1.3 |
| Calcium | | 9.4 mg/dL | 8.9–10.8 |
| Chloride | LO | 93 mEq/L | 97–109 |
| Creatinine | | 0.7 mg/dL | 0.6–1.4 |
| Glucose | HI | 270 mg/dL | 68–113 |
| Phosphatase, alkaline | | 62 IU/L | 23–140 |
| Potassium | | 4.4 mEq/L | 3.7–5.3 |
| Protein, total | | 7.7 g/dL | 6.1–8.2 |
| Sodium | LO | 131 mEq/L | 136–147 |
| Transferase (GOT) | HI | 70 IU/L | 4–39 |
| Urea Nitrogen | | 17 mg/dL | 7–24 |

EXAMPLE 3

Example 3 represents the unitized report in an enhanced manner, with the tests ranked highest to lowest. This example demonstrates the deletion of the reference ranges and their replacement with a ±1.0 unitized reference range. Also reported is the unitized analytical variation. These tests can be ranked because all of the tests have been unitized and the unitized results represent the true relationships among the tests. A greater enhancement of the data could be accomplished by color printing the background so that the higher normal values (greater +0.5 to +1.0) and the lower normal values (less than −0.5 to −1.0) would be in amber; mid normal ranges (−0.5 to +0.5) would be in green; abnormally low values would be in blue; and, abnormally high values would be in red, or in any other color enhanced schemes.

| UNITARY REPORT | | |
|---|---|---|
| TEST | RESULT | ±UAV |
| Bilirubin, total | HI +9.1 | 0.3 |
| Glucose | HI +7.8 | 0.2 |
| Transferase (GOT) | HI +2.7 | 0.2 |
| Protein, total | +0.5 | 0.1 |
| Urea Nitrogen | +0.2 | 0.2 |
| Potassium | −0.1 | 0.1 |
| Phosphatase, alkaline | −0.3 | 0.1 |
| Calcium | −0.5 | 0.1 |
| Creatinine | −0.7 | 0.1 |
| Albumin | LO −1.1 | 0.0 |

-continued

UNITARY REPORT

| TEST | RESULT | ±UAV |
|------|--------|------|
| Chloride | LO −1.5 | 0.2 |
| Sodium | LO −1.8 | 0.2 |

Reference Range = 0.0 ± 1.0
UAV = Unitized Analytical Variation

EXAMPLE 4

Example 4 represents the unitized data restructured to present the tests in a horizontal graphic format. The hierarchical ranking is retained. This manner of presentation is allowed due to the unitization of the data. The data could also be reversed ranked if desired. And, the background could be color enhanced, if desired.

UNITARY METHOD WITH GRAPH

| TEST | RESULT | ABN LO | LO ( NORMAL / | HI NORMAL ) | ABN HI |
|------|--------|--------|---------------|-------------|--------|
| Bili, T | HI +9.1 | :....(....:..../....:....)....: X |||||
| Glucose | HI +7.8 | :....(....:..../....:....)....: X |||||
| Trans(GOT) | HI +2.7 | :....(....:..../....:....)....: X |||||
| Prot, T | +0.5 | :....(....:..../....X....)....: |||||
| Urea N | +0.2 | :....(....:..../..X..:....)....: |||||
| Potassium | −0.1 | :....(....:...X/....:....)....: |||||
| Phos, Alk | −0.3 | :....(....:..X../....:....)....: |||||
| Calcium | −0.5 | :....(....X..../....:....)....: |||||
| Creat | −0.7 | :....(..X.:..../....:....)....: |||||
| Albumin | LO −1.1 | :...X(....:..../....:....)....: |||||
| Chloride | LO −1.5 | X....(....:..../....:....)....: |||||
| Sodium | LO −1.8 | X :....(....:..../....:....)....: |||||
|  |  | −1.0 | 0.0 | +1.0 ||

EXAMPLE 5

Example 5 displays a composite report including both the traditional report and the newly invented unitized report. This example represents the combining of Examples 2 and 3. In this manner the interpreter could compare the conventionally used reporting format with the new Unitary Report, without any loss of informational content. In this example the traditional report format has been altered to place the tests in the same rank that can be found in the Unitary Report. This minor rearrangement of the traditional alphabetically formatted data further enhances the interpreter's ability to compare the results.

COMBINED TRADITIONAL AND UNITARY REPORTS

Traditional Report

| TEST | RESULT | REFERENCE RANGE |
|------|--------|-----------------|
| Bilirubin, total | HI 6.2 mg/dL | 0.2–1.3 |
| Glucose | HI 270 mg/dL | 68–113 |
| Transferase (GOT) | HI 70 IU/L | 4–39 |
| Protein, total | 7.7 g/dL | 6.1–8.2 |
| Urea Nitrogen | 17 mg/dL | 7–24 |
| Potassium | 4.4 mEq/L | 3.7–5.3 |

-continued

COMBINED TRADITIONAL AND UNITARY REPORTS

| | | |
|---|---|---|
| Phosphatase, alkaline | 62 IU/L | 23–140 |
| Calcium | 9.4 mg/dL | 8.9–10.8 |
| Creatinine | 0.7 mg/dL | 0.6–1.4 |
| Albumin | LO 3.3 g/dL | 3.4–5.3 |
| Chloride | LO 93 mEq/L | 97–109 |
| Sodium | LO 131 mEq/L | 136–147 |

Unitary Report

| TEST | RESULT | ±UAV |
|------|--------|------|
| Bilirubin, total | HI +9.1 | 0.3 |
| Glucose | HI +7.8 | 0.2 |
| Transferase (GOT) | HI +2.7 | 0.2 |
| Protein, total | +0.5 | 0.1 |
| Urea Nitrogen | +0.2 | 0.2 |
| Potassium | −0.1 | 0.1 |
| Phosphatase, alkaline | −0.3 | 0.1 |
| Calcium | −0.5 | 0.1 |
| Creatinine | −0.7 | 0.1 |
| Albumin | LO −1.1 | 0.0 |
| Chloride | LO −1.5 | 0.2 |
| Sodium | LO −1.8 | 0.2 |

Reference Range = 0.0 ± 1.0
±UAV = ±Unitized Analytical Variation

EXAMPLE 6

Example 6 represents the traditional data and the graphed unitized data combined into a composite report. This example essentially combines Examples 2, 3, and 4 into one report, allowing maximal extraction of information from the data.

COMBINED TRADITIONAL AND UNITARY REPORTS
- WITH GRAPH

Traditional Report

| TEST | RESULT | REFERENCE RANGE |
|------|--------|-----------------|
| Bilirubin, total | HI 6.2 mg/dL | 0.2–1.3 |
| Glucose | HI 270 mg/dL | 68–113 |
| Transferase (GOT) | HI 70 IU/L | 4–39 |
| Protein, total | 7.7 g/dL | 6.1–8.2 |
| Urea Nitrogen | 17 mg/dL | 7–24 |
| Potassium | 4.4 mEq/L | 3.7–5.3 |
| Phosphatase, alkaline | 62 IU/L | 23–140 |
| Calcium | 9.4 mg/dL | 8.9–10.8 |
| Creatinine | 0.7 mg/dL | 0.6–1.4 |
| Albumin | LO 3.3 g/dL | 3.4–5.3 |
| Chloride | LO 93 mEq/L | 97–109 |
| Sodium | LO 131 mEq/L | 136–147 |

COMBINED TRADITIONAL AND UNITARY REPORTS - WITH GRAPH

UNITARY REPORT

| TEST | RESULT | | ABN LO ( | LO NORMAL / | HI NORMAL ) | ABN HI | |
|---|---|---|---|---|---|---|---|
| Bili, T | HI | +9.1 | :.....(....:..../....:....).....: | | | | X |
| Glucose | HI | +7.8 | :.....(....:..../....:....).....: | | | | X |
| Trans(GOT) | HI | +2.7 | :.....(....:..../....:....).....: | | | | X |
| Prot, T | | +0.5 | :.....(....:..../....X....)....: | | | | |
| Urea N | | +0.2 | :.....(....:..../.X..:....)....: | | | | |
| Potassium | | −0.1 | :.....(....:...X/....:....)....: | | | | |
| Phos, Alk | | −0.3 | :.....(.....:.X../....:....)....: | | | | |
| Calcium | | −0.5 | :.....(....X..../....:....)....: | | | | |
| Creat | | −0.7 | :.....(..X.:..../....:....)....: | | | | |
| Albumin | LO | −1.1 | :...X(....:..../....:....)....: | | | | |
| Chloride | LO | −1.5 | X....(....:..../....:....)....: | | | | |
| Sodium | LO | −1.8 | X :.....(....:..../....:....).....: | | | | |
| | | | −1.0 | 0.0 | +1.0 | | |

EXAMPLE 7

Example 7 illustrates the combination of two different styles of reporting unitized data, according to the present invention. The traditional reporting format has not been incorporated into this report. In some circumstances, it may not be necessary to utilize the traditional format.

UNITARY REPORT - TABULAR AND GRAPH

| TEST | RESULT | | | ±UAV |
|---|---|---|---|---|
| Bilirubin, total | HI | | +9.1 | 0.3 |
| Glucose | HI | | +7.8 | 0.2 |
| Transferase (GOT) | HI | | +2.7 | 0.2 |
| Protein, total | | | +0.5 | 0.1 |
| Urea Nitrogen | | | +0.2 | 0.2 |
| Potassium | | | −0.1 | 0.1 |
| Phosphatase, alkaline | | | −0.3 | 0.1 |
| Calcium | | | −0.5 | 0.1 |
| Creatinine | | | −0.7 | 0.1 |
| Albumin | | LO | −1.1 | 0.0 |
| Chloride | | LO | −1.5 | 0.2 |
| Sodium | | LO | −1.8 | 0.2 |

| TEST | RESULT | | ABN LO ( | LO NORMAL / | HI NORMAL ) | ABN HI | |
|---|---|---|---|---|---|---|---|
| Bili, T | HI | +9.1 | :.....(....:..../....:....).....: | | | | X |
| Glucose | HI | +7.8 | :.....(....:..../....:....).....: | | | | X |
| Trans(GOT) | HI | +2.7 | :.....(....:..../....:....).....: | | | | X |
| Prot, T | | +0.5 | :.....(....:..../....X....)....: | | | | |
| Urea N | | +0.2 | :.....(....:..../.X..:....)....: | | | | |
| Potassium | | −0.1 | :.....(....:...X/....:....)....: | | | | |
| Phos, Alk | | −0.3 | :.....(.....:.X../....:....)....: | | | | |
| Calcium | | −0.5 | :.....(....X..../....:....)....: | | | | |
| Creat | | −0.7 | :.....(..X.:..../....:....)....: | | | | |
| Albumin | LO | −1.1 | :...X(....:..../....:....)....: | | | | |
| Chloride | LO | −1.5 | X....(....:..../....:....)....: | | | | |
| Sodium | LO | −1.8 | X :.....(....:..../....:....).....: | | | | |
| | | | −1.0 | 0.0 | +1.0 | | |

EXAMPLE 8

This example illustrates the utilization of unitized data in the setting of repeat analyses of the same test. Both traditional and unitized data according to the present invention have been incorporated into the report. Also, day-to-day running averages of both types of data and a graphic report of the unitized data have been included. The data may also be presented without averaging or a cumulative type of running average may be used. The type of averaging used can be adapted to accommodate the user's requirements. Again, maximal information has been extracted from the primary data.

REPEAT ANALYSES OF THE SAME TEST

| | TRADITIONAL REPORT | | UNITARY REPORT | |
|---|---|---|---|---|
| TEST | RESULT | AVG | RESULT | AVG |
| Glucose | 270 | — | +7.8 | — |
| | 200 | 235 | +6.3 | +7.0 |
| | 160 | 180 | +3.9 | +5.1 |
| | 111 | 136 | +2.0 | +2.9 |
| | 94 | 103 | +0.5 | +1.2 |
| | 90 | 92 | +0.1 | +0.3 |
| | 89 | 90 | 0.0 | 0.0 |
| | 80 | 85 | −0.3 | −0.2 |
| | 78 | 79 | −0.5 | −0.4 |
| | 80 | 79 | −0.5 | −0.5 |
| REFERENCE RANGE | 68–113 | | −1.0–+1.0 | |

UNITARY GRAPHIC REPORT

| TEST | RESULT | ABN LO ( | LO NORMAL / | HI NORMAL ) | ABN HI | | AVG |
|---|---|---|---|---|---|---|---|
| | | −1.0 | 0.0 | +1.0 | | | |
| Glucose | HI +7.8 | ...(....:..../....:....)... | | | | X | — |
| | +6.3 | ...(....:..../....:....)... | | | | X | +7.0 |
| | +3.9 | ...(....:..../....:....)... | | | | X | +5.1 |
| | +2.0 | ...(....:..../....:....)... | | | | X | +2.9 |
| | +0.5 | ...(....:..../....X....)... | | | | | +1.2 |
| | +0.1 | ...(....:..../X..:....)... | | | | | +0.3 |
| | +0.0 | ...(....:....X....:....)... | | | | | 0.0 |
| | −0.3 | ...(.....:.X../....:....)... | | | | | −0.2 |
| | −0.5 | ...(....X..../....:....)... | | | | | −0.4 |
| | −0.5 | ...(....X..../....:....)... | | | | | −0.5 |

EXAMPLE 9

A vertical graphic presentation is illustrated in this example. As was mentioned in earlier examples, the background could be color enhanced. This type of presentation may be preferred in some settings.

EXAMPLE 9
VERTICAL GRAPH

| | sodium | chloride | albumin | creat | calcium | alk phos | potassium | urea nitr | t proteIn | transfer | glucose | t bili | | |
|---|---|---|---|---|---|---|---|---|---|---|---|---|---|---|
| +2.0 | | | | | | | | | | X | X | X | | |
| | — | — | — | — | — | — | — | — | — | — | — | — | | |
| | — | — | — | — | — | — | — | — | — | — | — | — | | |
| | — | — | — | — | — | — | — | — | — | — | — | — | | |
| +1.5 | | | | | | | | | | | | | | |
| | — | — | — | — | — | — | — | — | — | — | — | — | | |
| | — | — | — | — | — | — | — | — | — | — | — | — | | |
| | — | — | — | — | — | — | — | — | — | — | — | — | | |
| +1.0 | | | | | | | | | | | | | r | h |
| | — | — | — | — | — | — | — | — | — | — | — | — | e | i |
| | — | — | — | — | — | — | — | — | — | — | — | — | f | |
| | — | — | — | — | — | — | — | — | — | — | — | — | e | |
| | — | — | — | — | — | — | — | — | — | — | — | — | r | n |
| +0.5 | | | | | | | | X | | | | | e | o |
| | — | — | — | — | — | — | — | — | — | — | — | — | n | r |
| | — | — | — | — | — | — | — | — | — | — | — | — | c | m |
| | — | — | — | — | — | — | — | X | — | — | — | — | e | a |
| | — | — | — | — | — | — | — | — | — | — | — | — | . | l |
| 0.0 | | | | | | | | | | | | | . | . |
| | — | — | — | — | — | — | X | — | — | — | — | — | . | n |
| | — | — | — | — | — | — | — | — | — | — | — | — | . | o |
| | — | — | — | — | — | X | — | — | — | — | — | — | . | r |
| | — | — | — | — | — | — | — | — | — | — | — | — | . | m |
| -0.5 | | | | X | | | | | | | | | . | a |
| | — | — | — | — | — | — | — | — | — | — | — | — | r | l |
| | — | — | — | X | — | — | — | — | — | — | — | — | a | |
| | — | — | — | — | — | — | — | — | — | — | — | — | n | |
| | — | — | — | — | — | — | — | — | — | — | — | — | g | l |
| -1.0 | | | | | | | | | | | | | e | o |
| | — | — | X | — | — | — | — | — | — | — | — | — | | |
| | — | — | — | — | — | — | — | — | — | — | — | — | | |
| | — | — | — | — | — | — | — | — | — | — | — | — | | |
| -1.5 | | X | | | | | | | | | | | | |
| | — | — | — | — | — | — | — | — | — | — | — | — | | |
| | — | — | — | — | — | — | — | — | — | — | — | — | | |
| | X | — | — | — | — | — | — | — | — | — | — | — | | |
| -2.0 | | | | | | | | | | | | | | |

Comparative Pattern Analysis

According to another embodiment of the present invention, one or more medical conditions of a patient can be quickly and efficiently assessed utilizing unitized test values arranged in a predefined order to produce various patterns. The term "patient" as used herein includes all beings, both human and animal. It is understood that this aspect of the present invention is not limited to assessing medical conditions of patients. As described above, the present invention may be utilized to determine conditions of attributes of any type of object (biological and non-biological).

Figure 3:
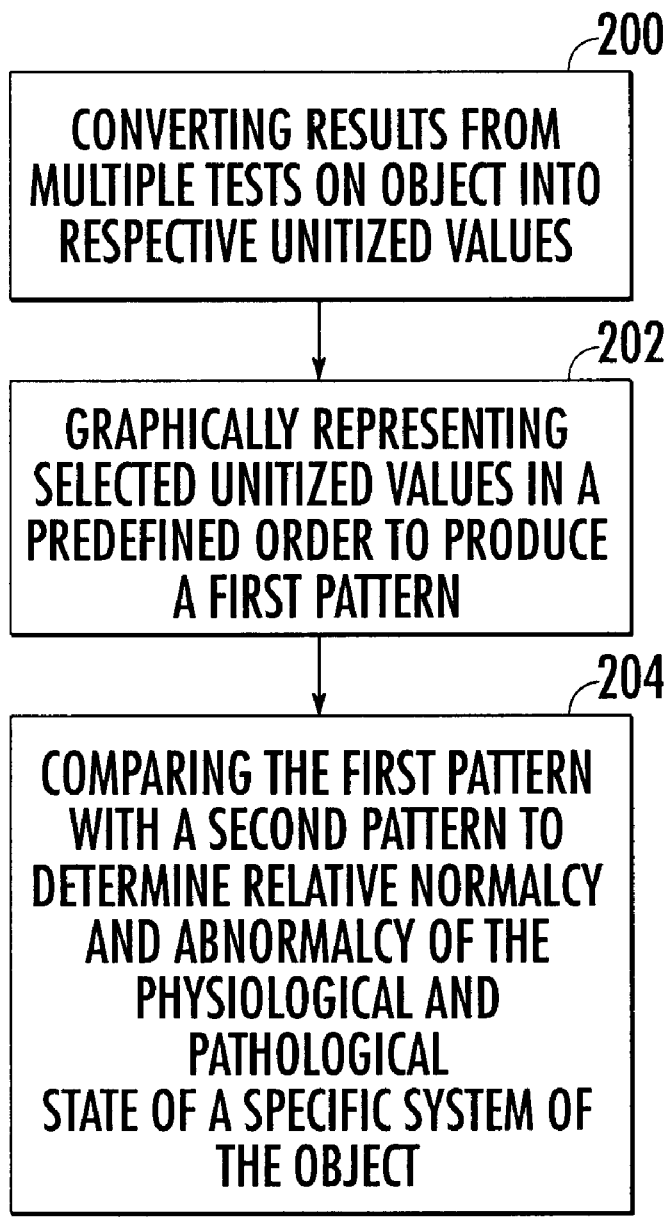
FIG. 3 schematically illustrates operations for assessing the medical condition of patients by comparing graphical representations of unitized data, according to an embodiment of the present invention.

Referring to FIG. 3, operations for implementing this aspect of the present invention within a data processing system are illustrated. Results from a plurality of medical tests on a patient are converted into a respective plurality of unitized values (Block 200). Preferably, each medical test conducted relates to some medical aspect of the patient and includes a respective reference range of test results associated therewith. As described above, each unitized value represents the relative normalcy or abnormalcy of a respective medical test result with respect to the reference range associated with a medical test. Operations for converting results for each medical test into a respective unitized value have been described above with respect to FIGS. 1 and 2.

Next, a data processing system graphically represents selected ones (i.e., any number from one to all) of the unitized values in a predefined order to produce a first pattern (Block 202). The term "selected ones" as used herein is understood to mean any number of unitized values, including all of the unitized values transformed from respective equilibrated values.

The data processing system then compares the first pattern with a known second pattern to determine relative normalcy and abnormalcy of medical conditions of a particular patient organ/system of interest (Block 204). It is understood that the term "relative normalcy and abnormalcy" is defined herein to include any other term of variation or measurement. Preferably, the second pattern is a graphical representation of the selected unitized values that indicates a normal medical condition of the specific system, or an established disease pattern of the specific system.

The term "second pattern", as used herein, refers to any one of many secondary patterns. In one application of a pattern comparative process according to an embodiment of the present invention, a first pattern may be compared with any number of secondary patterns until one or more of the secondary patterns represent a likely match or matches. Once the likely match or matches are determined, a statement suggesting likely diseases, other abnormalities or normalcy can be provided, based on the known identity of the secondary patterns. In another application of a pattern comparative process according to an embodiment of the present invention, any number of secondary patterns may be arbitrarily chosen. A numerical designation can be attached to each secondary pattern indicating the likelihood, probability or any other statistical appellation with which each secondary pattern represents a match to a first pattern. Furthermore, it is understood that the systems, methods, and computer program products herein described can produce these diagnostic matches and report them as an integral component of a report.

Preferably, the selected unitized values relate to medical conditions and/or aspects of a specific system of a patient, such as an organ or the blood system. For example, FIG. 4 illustrates medical test results in both a traditional reporting format and in the unitized format for the following groups: hydration, renal, bone, liver, metabolism and lytes. Some of the medical test results illustrated in FIG. 4 are used in more than one group because the test results have medical significance with respect to multiple groups. As illustrated in FIG. 4, each unitized value is represented in bar graph format. Viewing the unitized data as presented in FIG. 4, a user can quickly and easily assess the chemical status of multiple body organs and/or systems of a patient. For example, the medical condition of a patient's liver can be quickly assessed by comparing a pattern of unitized results for the listed liver tests with a pattern of unitized results for a normal liver.

Referring now to FIG. 5A, a hemogram 40 of test results and unitized test values and a corresponding hemograph 42a of the unitized test values are illustrated. In FIG. 5A, the hemograph 42a represents the unitized test results of the hemogram 40 in "bar graph" format. As illustrated, each bar extends from the origin axis (0.0) in a direction indicating whether a respective unitized test value is positive or negative. This pattern indicates the existence of macrocytic anemia. The individual unitized values as exemplified by their respective bar graphs for a macrocytic anemia will generally maintain similar relative positive and negative relationships even when the individual values vary in lesser or greater amounts, as can be seen in less severe or more severe macrocytic anemias. It is also understood that these same relationships between the unitized values may be seen in prodromal anemia when the individual values may have not become abnormal.

In FIG. 5B, the illustrated hemograph 42b represents the unitized data of the hemogram 40 (FIG. 5A) in bar graph format with each bar extending in the same direction. The hemograph 42b presents a distinct pattern that indicates the existence of macrocytic anemia, which is represented by an alternative distinct pattern that has resulted from repositioning the x-axis from 0.0 to −3.0. It is understood that individual tests can either be re-sorted; or, the x-axis can be repositioned to a value other than 0.0. When either of these changes is made, a distinct pattern will emerge that is consistent with macrocytic anemia. Consequently, different patterns for macrocytic anemia can be devised. Regardless of the pattern chosen, the pattern will be reproducible.

Referring to FIGS. 6A and 6B, hemographs 44, 46 that have distinct patterns indicating the existence of microcytic anemia and normocytic anemia, respectively, are illustrated. According to this embodiment of the present invention, medical tests that produce patterns similar to the hemographs 42b, 44, 46 of FIGS. 5B, 6A, 6B can be interpreted as representative of various types of anemia, without requiring detailed interpretation of the individual test data. Similarly, patterns of unitized values associated with medical tests related to other specific organs/body systems may be interpreted to diagnose a patient's medical condition.

Figure 7A:
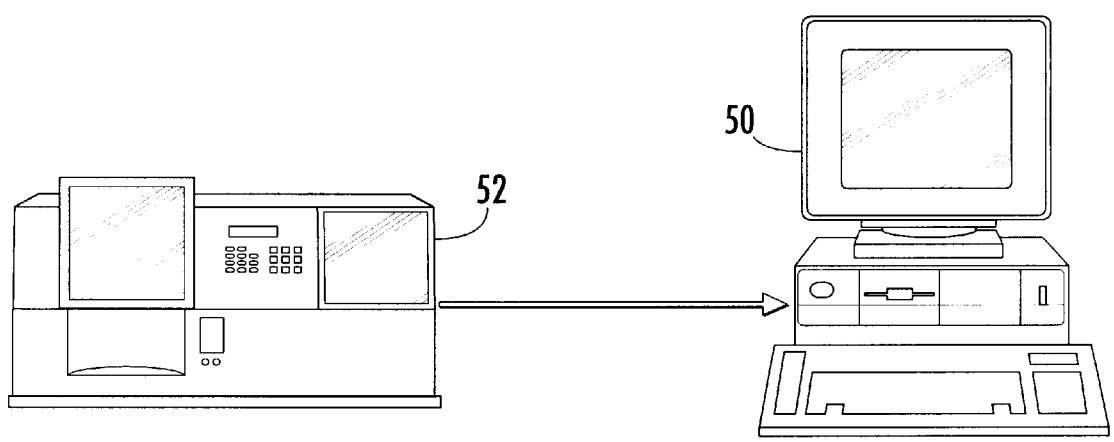
FIG. 7A illustrates an exemplary data processing system that is configured to receive test results from a medical analysis device and that is configured to perform the method steps illustrated in FIG. 3.

The various operations of the present invention (i.e., converting, graphically representing and comparing) may be performed by a discrete data processing system that receives test results as input. As illustrated in FIG. 7A, a data processing system 50 receives test results from a laboratory analysis device 52.

A laboratory (or other) analytical device can be any analytical system that produces a numerical value, as illustrated in Block 110 of FIG. 1. It is understood that analyzers are constantly in a state of change. Regardless of the design of any analyzer, the measured numerical result produced is suitable for unitization. Furthermore, the unitized values can be subjected to bar graph representation or other graphic representation. In addition, other mathematical manipulations, such as numeric ratios, can be performed using the unitized values. These graphic or numeric representations of measured values can be designated in a fixed order, or other configurations, which will yield distinct reproducible patterns or ratios that can be interpreted as representative of various types of normal, prodromal disease, or disease states. It is understood that the term "pattern" as used herein includes, but is not limited to, graphical and/or pictorial patterns or representations, as well as various types of displays of numeric ratios.

Figure 7B:
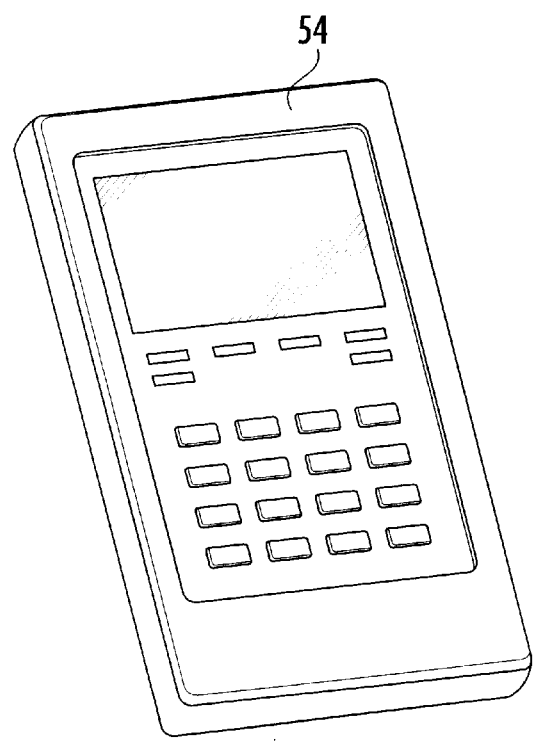
FIG. 7B illustrates an exemplary hand held diagnostic device containing a data processor that is configured to perform the method steps illustrated in FIG. 3.

Furthermore, the present invention may also be performed by a testing device configured to perform one or more of the medical tests. As illustrated in FIG. 7B, a hand held diagnostic device 54 contains a data processor for carrying out the present invention.

Preferably, operations according to the present invention are performed by a data processing system in real time. The present invention may be adapted for use with diagnosing the medical state of various types of living beings including, but not limited to, humans and animals. Also, the present invention may be adapted for use with diagnosing the condition of various types of objects by measuring and analyzing various attributes of objects. The term "attributes" refers to any type of characteristic, quality or condition of an object. By way of example, exemplary attributes of an object may be physical, such as material hardness, or numerical, such as the number of lines of code in a computer program. In addition, present invention may be adapted for use with any type of analytical device or system that produces numerical results.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clause are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of assessing a medical condition of a being, the method comprising the following steps that are performed in a data processing system:

obtaining results from a plurality of medical tests, wherein each medical test relates to a medical aspect of the being, and wherein each medical test includes a respective reference range of medical test results associated therewith;

unitizing singularly possible medical test results in a reference range associated with each medical test to a respective single number, wherein each reference range is bounded by upper and lower values of the reference range, wherein a single fractional value of each value in a reference range is equal to a single fractional value of every other value in the reference range, and wherein a sum of all fractional values equals the single number;

determining a total number of singularly possible medical test result within one or more respective portions of each reference range, comprising:

converting singularly possible test resulting the test results in the reference range having decimal value to a whole number;

determining a total number of singularly possible test results within the reference range to produce a reference range spread, comprising;

subtracting the lower value of the reference range from the upper value of the reference range; and adding an integer to the value obtained by subtracting the lower value of the reference range from the upper value of the reference range; and dividing the reference range spread in one or more respective portions;

transforming the results of each medical test into respective equilibrated values, wherein each equilibrated value represents a relative position of the results of a respective medical test with respect to a point of equilibration of a reference a range associated with the respective medical test so as to yield numerically like data values of the reference range;

transforming each of the equilibrated values into respective utilized values, wherein each unitized value represents relative normalcy or abnormalcy of a respective medical test result with respect to the upper and lower values of the reference range associated with the medical test;

graphically representing selected ones of the unitized values in a predefined order to produce a first pattern, wherein the selected unitized values relate to medical aspects of a specific system of the being; and comparing the first pattern with a second pattern to determine relative normalcy and abnormalcy of a medical condition of the specific system, wherein the second pattern comprises a graphical representation of the selected unitized values that indicates a medical condition of the specific system.

2. The method according to claim 1 wherein the step of transforming the results of each medical test into respective equilibrated values comprises the steps of:

determining a point of equilibration for each respective reference range; and determining a respective difference between each respective point of equilibration and the results of each respective medical test.

3. The method according to claim 1 wherein the step of transforming each of the equilibrated values into respective unitized values comprises multiplying each respective equilibrated value with a fractional value of a plurality of test results of a portion of a respective reference range.

4. The method according to claim 1 further comprising the step of determining a unitized analytical variation of each of the respective unitized values.

5. The method according to claim 1 wherein the step of graphically representing selected ones of the unitized values in a predefined order to produce a first pattern comprises the steps of displaying the unitized values with respective unitized reference ranges and unitized analytical variations.

6. The method according to claim 1 wherein the step of obtaining results from a plurality of medical tests comprises storing the results from the plurality of medical tests along with respective reference ranges in the data processing system.

7. The method according to claim 1 wherein the being is a human.

8. A data processing system for assessing a medical condition of a being, comprising:

means for obtaining results from a plurality of medical tests, wherein each medical test relates to a medical aspect of the being, and wherein each medical test includes a respective reference range of medical test results associated therewith;

means for unitizing singularly possible medical test results in a reference range associated with each medical test to a respective single number, wherein each reference range is bounded by upper and lower values of the reference range, wherein a single fractional value of each value in a reference range is equal to a single fractional value of every other value in the reference range, and wherein a sum of all fractional values equals the single number;

means for determining a total number of singularly possible medical test results within one or more respective portions of each reference range, comprising:

means for converting singularly possible test results in the reference range having a decimal value to a whole number;

means for determining a total number of singularly possible test results within the reference range to produce a reference range spread, comprising:

means for subtracting the lower value of the reference range from the upper value of the reference range; and means for adding an integer to the value obtained by subtracting the lower value of the reference range from the upper value of the reference range; and means for dividing the reference range spread in one or more respective portions;

means for transforming the results of each medical test into respective equilibrated values, wherein each equilibrated value represents a relative position of the results of a respective medical test with respect to a point of equilibration of a reference range associated with the respective medical test so as to yield numerically like data values when the data values are equally less than or greater than the respective lower and upper values of the reference range;

means for transforming each of the equilibrated values into respective unitized values, wherein each unitized value represents relative normalcy or abnormalcy of a respective medical test result with respect to the upper and lower values of the reference range associated with the medical test;

means for graphically representing selected ones of the unitized values in a predefined order to produce a first pattern, wherein the selected unitized values relate to medical aspects of a specific system of the being; and means for comparing the first pattern with a second pattern to determine relative normalcy and abnormalcy of a medical condition of the specific system, wherein the second pattern comprises a graphical representation of the selected unitized values that indicates a medical condition of the specific system.

9. The data processing system according to claim 13 wherein the means for transforming the results of each medical test into respective equilibrated values comprises:

means for determining a point of equilibration for each respective reference range; and means for determining a respective difference between each respective point of equilibration and the results of each respective medical test.

10. The data processing system according to claim 8 wherein the means for transforming each of the equilibrated values into respective unitized values comprises means for multiplying each respective equilibrated value with a fractional value of a plurality of test results of a portion of a respective reference range.

11. The data processing system according to claim 8 further comprising means for determining a unitized analytical variation of each of the respective unitized values.

12. The data processing system according to claim 8 wherein the means for graphically representing selected ones of the unitized values in a predefined order to produce a first pattern comprises means for displaying the unitized values with respective unitized reference ranges and unitized analytical variations.

13. The data processing system according to claim 8 wherein the means for obtaining results from a plurality of medical tests comprises means for storing the results from the plurality of medical tests along with respective reference ranges in the data processing system.

14. A computer program product for assessing a medical condition of a being, the computer program product comprising a computer usable storage medium having computer readable program code embodied in the medium, the computer readable program code comprising:

computer readable program code for obtaining results from a plurality of medical tests, wherein each medical test relates to a medical aspect of the being, and wherein each medical test includes a respective reference range of medical test results associated therewith;

computer readable program code for unitizing singularly possible medical test results in a reference range associated with each medical test to a respective single number, wherein each reference range is bounded by upper and lower values of the reference range, wherein a single fractional value of each value in a reference range is equal to a single fractional value of every other value in the reference range, and wherein a sum of all fractional values equals the single number;

computer readable program code for determining a total number of singularly possible medical test results within one or more respective portions of each reference range, comprising;

computer readable program code for converting singularly possible test results in the reference range having a decimal value to a whole number;

computer readable program code for determining a total number of singularly possible test results within the reference range to produce a reference range spread, comprising:

computer readable program code for subtracting the lower value of the reference range from the upper value of the reference range; and computer readable program code for adding an integer to the value obtained by subtracting the lower value of the reference range from the upper value of the reference range; and computer readable program code for dividing the reference range spread in one or more respective portions;

computer readable program code for transforming the results of each medical test into respective equilibrated values, wherein each equilibrated value represents a relative position of the results of a respective medical test with respect to a point of equilibration of a reference range associated with the respective medical test so as to yield numerically like data values when the data values are equally less than or greater than the respective lower and upper values of the reference range;

computer readable program code for transforming each of the equilibrated values into respective unitized values, wherein each unitized value represents relative normalcy or abnormalcy of a respective medical test result with respect to the upper and lower values of the reference range associated with the medical test;

computer readable program code for graphically representing selected ones of the unitized values in a predefined order to produce a first pattern, wherein the selected unitized values relate to medical aspects of a specific system of the being; and computer readable program code for comparing the first pattern with a second pattern to determine relative normalcy and abnormalcy of a medical condition of the specific system, wherein the second pattern comprises a graphical representation of the selected unitized values that indicates a medical condition of the specific system.

15. The computer program product according to claim 14 wherein the computer readable program code for transforming the results of each medical test into respective equilibrated values comprises:

computer readable program code for determining a point of equilibration for each respective reference range; and computer readable program code for determining a respective difference between each respective point of equilibration and the results of each respective medical test.

16. The computer program product according to claim 14 wherein the computer readable program code for transforming each of the equilibrated values into respective unitized values comprises computer readable program code for multiplying each respective equilibrated value with a fractional value of a plurality of test results of a portion of a respective reference range.

17. The computer program product according to claim 14 further comprising computer readable program code for determining a unitized analytical variation of each of the respective unitized values.

18. The computer program product according to claim 14 wherein the computer readable program code for graphically representing selected ones of the unitized values in a predefined order to produce a first pattern comprises computer readable program code for displaying the unitized values with respective unitized reference ranges and unitized analytical variations.

19. The computer program product according to claim 14 wherein the computer readable program code for obtaining results from a plurality of medical tests comprises computer readable program code for storing the results from the plurality of medical tests along with respective reference ranges in the data processing system.

20. A method of assessing a condition of an object, the method comprising the following steps that are performed in a data processing system:

obtaining results from a plurality of tests performed on the object, wherein each test relates to an attribute of the object, and wherein each test includes a respective reference range of test results associated therewith;

unitizing singularly possible test results in a reference range associated with each test to a respective single number, wherein each reference range is bounded by upper and lower values of the reference range, wherein a single fractional value of each value in a reference range is equal to a single fractional value of every other value in the reference range, and wherein a sum of all fractional values equals the single number;

determining a total number of singularly possible test results within one or more respective portions of each reference range, comprising;

converting singularly possible test results in the reference range having a decimal value to a whole number;

determining a total number of singularly possible test results within the reference range to produce a reference range spread, comprising:

subtracting the lower value of the reference range from the upper value of the reference range; and adding an integer to the value obtained by subtracting the lower value of the reference range from the upper value of the reference range; and dividing the reference range spread in one or more respective portions;

transforming the results of each test into respective equilibrated values, wherein each equilibrated value represents a relative position of the results of a respective test with respect to a point of equilibration of a reference range associated with the respective test so as to yield numerically like data values when the data values are equally less than or greater than the respective lower and upper values of the reference range;

transforming each of the equilibrated values into respective unitized values, wherein each unitized value represents relative normalcy or abnormalcy of a respective test result with respect to the upper and lower values of the reference range associated with the test;

graphically representing selected ones of the unitized values in a predefined order to produce a first pattern, wherein the selected unitized values relate to attributes of the object; and comparing the first pattern with a second pattern to determine relative normalcy and abnormalcy of a condition of the object, wherein the second pattern comprises a graphical representation of the selected unitized values that indicates a condition of the object.

21. The method according to claim 20 wherein the step of transforming the results of each test into respective equilibrated values comprises the steps of:

determining a point of equilibration for each respective reference range; and determining a respective difference between each respective point of equilibration and the results of each respective test.

22. The method according to claim 20 wherein the step of transforming each of the equilibrated values into respective unitized values comprises multiplying each respective equilibrated value with a fractional value of a plurality of test results of a portion of a respective reference range.

23. The method according to claim 20 further comprising the step of determining a unitized analytical variation of each of the respective unitized values.

24. The method according to claim 20 wherein the step of graphically representing selected ones of the unitized values in a predefined order to produce a first pattern comprises the steps of displaying the unitized values with respective unitized reference ranges and unitized analytical variations.

25. The method according to claim 20 wherein the step of obtaining results from a plurality of tests comprises storing the results from the plurality of tests along with respective reference ranges in the data processing system.

26. A data processing system for assessing a condition of an object, comprising:

means for obtaining results from a plurality of tests, wherein each test relates to an attribute of the object, and wherein each test includes a respective reference range of test results associated therewith;

means for unitizing singularly possible test results in a reference range associated with each test to a respective single number, wherein each reference range is bounded by upper and lower values of the reference range, wherein a single fractional value of each value in a reference range is equal to a single fractional value of every other value in the reference range, and wherein a sum of all fractional values equals the single number;

means for determining a total number of singularly possible test results within one or more respective portions of each reference range, comprising:

means for converting singularly possible test results in the reference range having a decimal value to a whole number;

means for determining a total number of singularly possible test results within the reference range to produce a reference range spread, comprising:

means for subtracting the lower value of the reference range from the upper value of the reference range; and means for adding an integer to the value obtained by subtracting the lower value of the reference range from the upper value of the reference range; and means for dividing the reference range spread in one or more respective portions;

means for transforming the results of each test into respective equilibrated values, wherein each equilibrated value represents a relative position of the results of a respective test with respect to a point of equilibration of a reference range associated with the respective test so as to yield numerically like data values when the data values are equally less than or greater than the respective lower and upper values of the reference range;

means for transforming each of the equilibrated values into respective unitized values, wherein each unitized value represents relative normalcy or abnormalcy of a respective test result with respect to the upper and lower values of the reference range associated with the test;

means for graphically representing selected ones of the unitized values in a predefined order to produce a first pattern, wherein the selected unitized values relate to attributes of the object; and means for comparing the first pattern with a second pattern to determine relative normalcy and abnormalcy of a condition of the object, wherein the second pattern comprises a graphical representation of the selected unitized values that indicates a condition of the object.

27. The data processing system according to claim 26 wherein the means for transforming the results of each test into respective equilibrated values comprises:

means for determining a point of equilibration for each respective reference range; and means for determining a respective difference between each respective point of equilibration and the results of each respective test.

28. The data processing system according to claim 26 wherein the means for transforming each of the equilibrated values into respective unitized values comprises means for multiplying each respective equilibrated value with a fractional value of a plurality of test results of a portion of a respective reference range.

29. The data processing system according to claim 26 further comprising means for determining a unitized analytical variation of each of the respective unitized values.

30. The data processing system according to claim 26 wherein the means for graphically representing selected ones of the unitized values in a predefined order to produce a first pattern comprises means for displaying the unitized values with respective unitized reference ranges and unitized analytical variations.

31. A computer program product for assessing a condition of an object, the computer program product comprising a computer usable storage medium having computer readable program code embodied in the medium, the computer readable program code comprising:

computer readable program code for obtaining results from a plurality of tests, wherein each test relates to an attribute of the object, and wherein each test includes a respective reference range of test results associated therewith;

computer readable program code for unitizing singularly possible test results in a reference range associated with each test to a respective single number, wherein each reference range is bounded by upper and lower values of the reference range, wherein a single fractional value of each value in a reference range is equal to a single fractional value of every other value in the reference range, and wherein a sum of all fractional values equals the single number;

computer readable program code for determining a total number of singularly possible test results within one or more respective portions of each reference range, comprising:

computer readable program code for converting singularly possible test results in the reference range having a decimal value to a whole number;

computer readable program code for determining a total number of singularly possible test results within the reference range to produce a reference range spread, comprising:

computer readable program code for subtracting the lower value of the reference range from the upper value of the reference range; and computer readable program code for adding an integer to the value obtained by subtracting the lower value of the reference range from the upper value of the reference range; and computer readable program code for dividing the reference range spread in one or more respective portions;

computer readable program code for transforming the results of each test into respective equilibrated values, wherein each equilibrated value represents a relative position of the results of a respective test with respect to a point of equilibration of a reference range associated with the respective test so as to yield numerically like data values when the data values are equally less than or greater than the respective lower and upper values of the reference range;

computer readable program code for transforming each of the equilibrated values into respective unitized values, wherein each unitized value represents relative normalcy or abnormalcy of a respective test result with respect to the upper and lower values of the reference range associated with the test;

computer readable program code for graphically representing selected ones of the unitized values in a predefined order to produce a first pattern, wherein the selected unitized values relate to attributes of the object; and computer readable program code for comparing the first pattern with a second pattern to determine relative normalcy and abnormalcy of a condition of the object, wherein the second pattern comprises a graphical representation of the selected unitized values that indicates a condition of the object.

32. The computer program product according to claim 31 wherein the computer readable program code for transforming the results of each test into respective equilibrated values comprises:

computer readable program code for determining a point of equilibration for each respective reference range; and computer readable program code for determining a respective difference between each respective point of equilibration and the results of each respective test.

33. The computer program product according to claim 31 wherein the computer readable program code for transforming each of the equilibrated values into respective unitized values comprises computer readable program code for multiplying each respective equilibrated value with a fractional value of a plurality of test results of a portion of a respective reference range.

34. The computer program product according to claim 31 further comprising computer readable program code for determining a unitized analytical variation of each of the respective unitized values.

35. The computer program product according to claim 31 wherein the computer readable program code for graphically representing selected ones of the unitized values in a predefined order to produce a first pattern comprises computer readable program code for displaying the unitized values with respective unitized reference ranges and unitized analytical variations.

36. A testing device for assessing a condition of an object, comprising:

means for obtaining results from a plurality of tests, wherein each test relates to an attribute of the object, and wherein each test includes a respective reference range of test results associated therewith;

computer readable program code for unitizing singularly possible normal test results in a reference range associated with each test to a respective single number, wherein each reference range is bounded by upper and lower values of the reference range, wherein a single fractional value of each value in a reference range is equal to a single fractional value of every other value in the reference range, and wherein a sum of all fractional values equals the single number;

computer readable program code for determining a total number of singularly possible test results within one or more respective portions of each reference range, comprising:

computer readable program code for converting singularly possible test results in the reference range having a decimal value to a whole number;

computer readable program code for determining a total number of singularly possible test results within the reference range to produce a reference range spread, comprising:

computer readable program code for subtracting the lower value of the reference range from the upper value of the reference range; and computer readable program code for adding an integer to the value obtained by subtracting the lower value of the reference range from the upper value of the reference range; and computer readable program code for dividing the reference range spread in one or more respective portions;

computer readable program code for transforming the results of each test into respective equilibrated values, wherein each equilibrated value represents a relative position of the results of a respective test with respect to a point of equilibration of a reference range associated with the respective test so as to yield numerically like data values when the data values are equally less than or greater than the respective lower and upper values of the reference range;

computer readable program code for transforming each of the equilibrated values into respective unitized values, wherein each unitized value represents relative normalcy or abnormalcy of a respective test result with respect to the upper and lower values of the reference range associated with the test;

computer readable program code for graphically representing selected ones of the unitized values in a predefined order to produce a first pattern, wherein the selected unitized values relate to attributes of the object; and computer readable program code for comparing the first pattern with a second pattern to determine relative normalcy and abnormalcy of a condition of the object, wherein the second pattern comprises a graphical representation of the selected unitized values that indicates a condition of the object.

37. The testing device according to claim 36 wherein the computer readable program code for transforming the results of each test into respective equilibrated values comprises:

computer readable program code for determining a point of equilibration for each respective reference range; and computer readable program code for determining a respective difference between each respective point of equilibration and the results of each respective test.

38. The testing device according to claim 36 wherein the computer readable program code for transforming each of the equilibrated values into respective unitized values comprises computer readable program code for multiplying each respective equilibrated value with a fractional value of a plurality of test results of a portion of a respective reference range.

39. The testing device according to claim 36 further comprising computer readable program code for determining a unitized analytical variation of each of the respective unitized values.

40. The testing device according to claim 36 wherein the computer readable program code for graphically representing selected ones of the unitized values in a predefined order to produce a first pattern comprises computer readable program code for displaying the unitized values with respective unitized reference ranges and unitized analytical variations.

* * * * *

UNITED STATES PATENT AND TRADEMARK OFFICE
CERTIFICATE OF CORRECTION

PATENT NO. : 6,500,117 B1
DATED : December 31, 2002
INVENTOR(S) : Hancock, Jr.

It is certified that error appears in the above-identified patent and that said Letters Patent is hereby corrected as shown below:

Column 23,
Line 21, should read -- test results within one or more respective portions of --
Line 23, should read -- converting singularly possible test --

Column 25,
Line 13, should read -- 9. The data processing system according to claim 8 --

Signed and Sealed this

Sixteenth Day of December, 2003

JAMES E. ROGAN
*Director of the United States Patent and Trademark Office*